United States Patent [19]
Hengstenberg

[11] Patent Number: 5,863,799
[45] Date of Patent: Jan. 26, 1999

[54] ERYTHROCYTE SEDIMENTATION RATE CONTROL

[75] Inventor: Wayne R. Hengstenberg, Clark, N.J.

[73] Assignee: Hycor Biomedical, Inc., Irvine, Calif.

[21] Appl. No.: 924,352

[22] Filed: Sep. 5, 1997

Related U.S. Application Data

[62] Division of Ser. No. 538,959, Oct. 4, 1995.

[51] Int. Cl.⁶ .................................................. G01N 15/04
[52] U.S. Cl. ................................ 436/10; 436/8; 436/70; 73/61.65; 600/370
[58] Field of Search .................... 436/8, 10, 11, 436/16, 18, 68, 70; 435/2; 252/408.1; 600/370; 73/61.65

[56] References Cited

U.S. PATENT DOCUMENTS

| | | | |
|---|---|---|---|
| 2,102,785 | 12/1937 | Brooks | 431/70 |
| 2,727,838 | 12/1955 | Dalter | 127/36 |
| 2,848,368 | 8/1958 | Witt | 73/61.65 |
| 2,929,764 | 3/1960 | Hultin et al. | 514/59 |
| 3,660,037 | 5/1972 | Sokol | 422/73 |
| 3,873,467 | 3/1975 | Hunt | 436/10 |
| 4,064,118 | 12/1977 | Wong | 530/385 |
| 4,102,810 | 7/1978 | Armstrong | 436/16 |
| 4,264,470 | 4/1981 | Chastain, Jr. et al. | 436/10 |
| 4,299,726 | 11/1981 | Crews et al. | 436/10 |
| 4,324,686 | 4/1982 | Mundschenk | 436/10 |
| 4,358,394 | 11/1982 | Crew et al. | 436/10 |
| 4,436,821 | 3/1984 | Ryan | 436/10 |
| 4,489,162 | 12/1984 | Hawkins et al. | 436/10 |
| 4,572,899 | 2/1986 | Walker et al. | 436/18 |
| 4,704,364 | 11/1987 | Carver et al. | 436/10 |
| 4,777,139 | 10/1988 | Wong et al. | 436/18 |
| 5,316,729 | 5/1994 | Orth et al. | 422/73 |
| 5,380,664 | 1/1995 | Carver et al. | 436/10 |
| 5,529,933 | 6/1996 | Young et al. | 436/10 |

OTHER PUBLICATIONS

Bull et al., *The Zeta Sedimentation Ratio*, Blood, 40(4):550 (Oct. 1972).

de Castro et al., *Valoracion de un sistema alternativo totalmente automatizado para la determinacion de la velocidad de sedimentacion globular*, Sangre 34(1):4–9 (1989).

International Committee for Standardization in Haematology (ICSH), *Guidelines on selection of laboratory tests for monitoring the acute phase response*, J. Clin. Pathol. 41:1203–1212 (1988).

International Committee for Standardization in haematology (ICSH), *Recommendation for Measurement of Erythrocyte Sedimentation Rate of Human Blood*, Am. J. Clin. Pathol. 68:505–512 (1981).

International Committee for Standardization in Haematology (ICSH), *Reference Method for the Erthrocyte Sedimentation Rate (ESR) Test on Human Blood*, Br.J. Haematol. 24:671 (1972).

Jou et al. *Evalucion de un sistema totalmente automatico para realizar la velocidad de sedimentacion globular*, Sangre 33:474–478 (1988).

Product Brochure, Dispette®, Ulster Scientific, Inc., New Paltz, NY, date unknown.

Product Brochure, Dispette®2, Ulster Scientific, Inc., New Paltz, NY, date unknown.

Todd–Sanford Clinical Diagnosis by Laboratory Method (15th edition), *Erythrocyte Sedentimation Rate*(ESR, edited by Davidsohn, I., and Henry, J., pp. 133–135, WB Sauders Company, London, Toronto (1974).

*Primary Examiner*—Maureen M. Wallenhorst
*Attorney, Agent, or Firm*—Lyon & Lyon LLP

[57] ABSTRACT

A three-phase solution suitable for use as an erythrocyte sedimentation rate control having the following three components: (1) a synthetic plasma base, (2) a high molecular weight polymer, and (3) mammalian red blood cells. The control is designed to allow the user to monitor the accuracy and precision of analytical methods for determining the sedimentation rate of human erythrocytes in whole blood specimens.

9 Claims, No Drawings

ERYTHROCYTE SEDIMENTATION RATE CONTROL

This is a divisional of application Ser. No. 08/538,959, filed on Oct. 4, 1995, pending.

FIELD OF THE INVENTION

This invention relates to the measurement of erythrocyte sedimentation rate (ESR), and more particularly to a blood control standard for the quality control of the measurement of ESR.

BACKGROUND OF THE INVENTION

The ESR test measures the sedimentation rate of aggregated erythrocytes in plasma. The rate of sedimentation is an indirect means of quantitating Rouleaux formation as well as red cell aggregation. Sedimentation occurs because the apparent surface/volume ratio of the red cells decreases and the denser Rouleaux overcome the buoyant forces of the plasma and sink. Erythrocyte sedimentation depends upon an interrelationship of a number of inherent biologic variables. Anything that increases the tendency to form Rouleaux or red cell aggregation will accelerate the sedimentation rate. In vivo, the plasma concentrations of proteins and globulins as well as the shape of the red blood cells are the most important factors contributing to the ESR.

In most normal persons, sedimentation takes place slowly, but in a variety of disease states the rate is rapid and in some cases proportional to the severity of the disease. The ESR test has been utilized as an indirect measure of these disease states. However, the test is very non-specific in that values for "normal" ESR may be influenced by local conditions as well as the age and sex of the patient. Nonetheless, the ESR test is an extremely common test which plays a significant role in contemporary medical practice.

Westergren developed the technique of performing an ESR determination as described in a paper published in 1924. See Alf Westergren, "Die senkungscreaktion", Ergegn. Inn. Med. Kinderheilk., 26:577 (1924). In the Westergren method, a blood sample is obtained by venepuncture and is thoroughly mixed with a suitable anticoagulant. Because the proteins and globulins in blood are unstable in vitro, at room temperature the test must be set up within 2 hours, or at 4° C. within 6 hours. The blood-anticoagulant is thoroughly mixed by gentle repeated inversion and a clean dry standard Westergren-Katz tube is filled and adjusted to the '0' mark. The tube is then placed in a strictly vertical position under room temperature conditions (18°–25° C.), not exposed to direct sunlight and free from vibrations and drafts. After a time period, usually 1 hour, the distance (x) from the bottom of the surface meniscus to the top of the column of sedimenting red cells (where the full density is apparent), is read in mm and recorded as the ESR value. The result is expressed as follows: 'ESR (Westergren 1 hr)=x mm'. Variations in the materials and methods are known, however, the basic technique is relatively unchanged since its introduction.

Due to the manner in which ESR is measured, in addition to the biologic variables certain identifiable environmental and technical factors may influence the ESR test in misleading ways. For example, the following factors may affect the measurement of ESR:

Environmental Factors

1. Temperature. The room temperature during the test could lead to a misleadingly high ESR (higher temperatures) or low ESR (lower temperatures). Further, a variation of temperature during the test will also lead to misleading results.

2. Vibration. Vibration or movement of the testing apparatus during the test will result in misleading results.

Procedural Factors

1. Positioning of tube. The correct or incorrect positioning of the tube at a perpendicular angle will affect test results.

2. Delay prior to test. A delay in performing the test beyond 2 hours of drawing the blood sample will create ambiguous results.

3. Insertion of tube in reservoir (for modified Westergren procedures). Failure to fully insert the tube to the bottom of the reservoir in certain modified Westergren procedures will affect the test results.

4. Unfamiliarity or failing to follow manufacturer's directions will affect test results.

Testing Materials Factors

1. Tube. Variations of the composition and/or length of the measurement tube will affect test results. For example, the use of glass vs. plastic tubes in either a Wintrobe or Westergren procedure will lead to variations in the observed sedimentation rate.

2. Anticoagulant. The anticoagulant used will affect test results.

3. Plasma. Changes in the plasma composition is a significant factor determining the measured ESR.

There currently is no known commercial control by which the foregoing, and other, factors can be eliminated as sources affecting test results. Accordingly, a given ESR measurement can only be accepted as within a relatively large range of error. This decreases the significance of the ESR test.

SUMMARY OF THE INVENTION

The present invention is a reference control designed to monitor the accuracy and precision of analytical methods for determining the sedimentation rate of human erythrocytes in whole blood specimens. The ESR control comprises a three component colloidal/emulsion suspension: (1) a synthetic plasma base, (2) a polymer having a high molecular weight in the range of between 15,000–500,000, and (3) mammalian red blood cells. In the referred embodiment, the polymer used is Dextran, a polysaccharide. Dextran is known for its use as a plasma expander used for cell separation, but is used for a different purpose in the ESR control of the present invention. Here, the addition of Dextran to the synthetic plasma base serves the function of behaving similar to an abnormal increase of large plasma proteins such as Fibrinogen and Alpha 2 macro-globulins in whole blood. It has been proposed that abnormal increases in plasma protein concentrations cause an increase in aggregate formation resulting in an increased ESR. The Dextran and synthetic plasma base is a stable suspension that maintains the morphology of the red cells for long periods of time to allow for a controlled sedimentation of the cells. An ESR measurement using the ESR control should fall within a fairly narrow, predictable range. Measurements outside this range would therefore indicate flaws in the testing method.

DETAILED DESCRIPTION OF THE PREFERRED EMBODIMENT

A number of subheadings are provided in the following discussion in order to provide organization and clarity.

1. Background and Theory

The ESR control of the present invention can be better understood if certain aspects of the phenomenon of sedimentation of erythrocytes in whole blood are described. Accordingly, a discussion of erythrocyte sedimentation and the theory of the ESR control are presented.

As previously discussed, the composition of the plasma is one of the two most important factors in determining erythrocyte sedimentation rate (the other being the shape of the red blood cells). The components in the plasma which create the Rouleaux effect and red cell aggregation are the plasma proteins and colloids, particularly the Fibrinogen, Alpha 1 and Alpha 2 globulins found in whole blood. It is known that all proteins affect the dielectric coefficient of plasma, but asymmetrical macromolecules are oriented by the field and hence exert a disproportionately large effect. Therefore, as fibrinogen and gamma globulin in plasma increase, they decrease the zeta potential of suspended red cells, permitting increased rouleaux formation and more rapid sedimentation rate. See Brian S. Bull and J. Douglas Brailsford, "The Zeta Sedimentation Ratio", *Blood* 1972:40:550. The ideal control would therefore incorporate these colloids and proteins. However, the chemistry of these components makes them unstable for any extended period of time, and would therefore limit the useful life of a control that included these components.

The use of a high molecular weight polymer such as Dextran in a synthetic plasma base serves to mimic the function of the Fibrinogen, Alpha 1 and Alpha 2 globulins found in whole blood by creating the Rouleaux effect. The two-phase Dextran/synthetic plasma suspension therefore behaves similarly to natural plasma with the advantage of being a stable compound. Unlike the plasma proteins and colloids, Dextran is stable in synthetic plasma.

The second important factor in accelerated erythrocyte sedimentation is the morphology of the cells. As fresh cells are allowed to sit in an EDTA or Sodium Citrate solution, they tend to crenate and manifest the phenomenon of anisocytosis and poikilocytosis along with exhibiting changes in the electrical charges on the surfaces of the red cells. Each of these changes tends to inhibit the sedimentation velocity. However, the Dextran/synthetic plasma base suspension has been found to maintain the morphology of pre-treated, stabilized cells for long periods of time to allow for a controlled precipitation of the erythrocytes. The synthetic plasma base which bathes the mammalian red cells appears to cause no variation of size and shape of the cells, thereby allowing the cells to maintain a constant morphology.

2. Components, Composition, and Method of Making

Turning now to the components and composition of the ESR control of the present invention, the control comprises a three component colloidal/emulsion suspension: (1) a synthetic plasma base, (2) a polymer having a high molecular weight substantially in the range of between 15,000–500,000, and (3) pre-treated, stabilized mammalian red blood cells. The three component colloidal/emulsion suspension is intended for use as a control for a given ESR test apparatus and method.

The ESR control is intended to exhibit the characteristics of a sample of human blood for the purpose of performing an ESR test. The components of the ESR control are therefore formulated to mimic these characteristics of human blood, such that there is provided a suspension that simulates an actual patient sample and that produces reproducible sedimentation rates within a predictable range of values. A commercially useful embodiment of the ESR control is further advantageously formulated to be stable for periods of prolonged storage.

The synthetic plasma base component of the ESR control is a carrying media that substitutes for plasma in natural blood and that maintains a homeostatic environment for the other components of the ESR control, particularly the red blood cells. For use in the ESR control, the synthetic plasma base comprises a carrying media that, in conjunction with the other components of the ESR control, produces predictable and reproducible red blood cell sedimentation rate values for a given ESR testing apparatus and method. In commercial ESR control products, it is preferable that the synthetic plasma base be formulated to stabilize the red blood cells and to maintain the morphology and specific gravity of the red blood cells, thereby conferring long-term stability on the ESR control.

To produce predictable and reproducible sedimentation rates in the ESR control, it has been found that Alsever's solution or a modified Alsever's solution-type synthetic plasma base is suitable for use as the synthetic plasma base component. It has been found that an ESR control having Alsever's solution as the synthetic plasma base component does not form a colloidal emulsion/suspension since the high molecular weight polymer component tends to dissolve in the Alsever's solution, however, this occurrence does not significantly effect the performance of the ESR control. An ESR control which relies substantially on Alsever's solution as the synthetic plasma base will be suitable if the requisite stability does not exceed a few days. Alsever's solution is a transport media well known in the art, comprising 2.05 gm dextrose, 0.80 gm sodium citrate, 0.42 gm sodium chloride, and 0.05 gm citric acid in 100 ml distilled water. Alsever's solution is well known as a media having preservative properties and that is useful for suspending living cells or tissues under investigation in vitro. As noted, the use of Alsever's solution as the synthetic plasma base component will provide an ESR control that produces predictable and reproducible ESR measurements, however, in an ESR control product with extended shelf life, it is advantageous to provide an altered formulation for the synthetic plasma base which includes components which are known to provide improved cell stability and prolonged shelf life.

For example, the addition of buffers to the synthetic plasma base has been found to assist in maintenance of a relatively constant pH. Bactericides and fungicides may be added to assist in retarding the adverse effects of contamination prior to or during storage. Protein stabilizers and cryoprotectants may be added to contribute to cell stability. Those skilled in the art will recognize that these and other materials may be added to the synthetic plasma base to provide additional beneficial results while not inhibiting the performance of the ESR control.

Accordingly, as a practical matter it is preferable to include materials in the synthetic plasma base that contribute to the long-term stability of the ESR control. To achieve this end, the synthetic plasma base is provided with materials that maintain the morphology and integrity of the red blood cells to allow the red blood cells to mimic the behavior of red blood cells in vivo, and to do so even after prolonged periods of storage. In relation to the interaction between the synthetic plasma base and the red blood cells, the properties of a synthetic plasma base which make it suitable for use in a commercially practical ESR control are the following: (1) the synthetic plasma base stabilizes the red blood cells in a manner that maintains the cell membranes in a dynamic state, (2) the synthetic plasma base maintains the morphology of the red blood cells, and (3) the synthetic plasma base maintains the specific gravity of the red blood cells.

A preferred form of the synthetic plasma base for use in the commercially practical ESR control is a synthetic plasma base that is provided with one or more of the materials described above, such as antibiotics, antifungals, protein stabilizers, cryoprotectants, and buffers. The synthetic plasma base is preferably formulated to exhibit characteristics similar to human plasma, such as specific gravity, pH, and potassium and sodium ion concentrations.

An example of a synthetic plasma base having the above-described properties which has been found to be suitable for use in the ESR control is the synthetic plasma base having the formulation listed below in Table 1. The synthetic plasma base having the formulation described in Table 1 has been found to confer long term stability to the red blood cells in the ESR control. Those skilled in the art will recognize that other and further variations of this formulation will provide the properties referred to above that make a solution suitable for use as the synthetic plasma base of the ESR control.

TABLE 1

Synthetic Plasma Base For Use in ESR Control

| Component | Amount Per Batch |
| --- | --- |
| Distilled Water | 40 L |
| Reagent Alcohol | 1,400 ml |
| Sodium Chloride | 40 gm |
| Sodium Fluoride | 30 gm |
| Sodium Citrate | 288 gm |
| Citric Acid | 20 gm |
| Sodium Nitrate | 200 gm |
| 3-N-morpholino propane sulfonic acid (MOPS) | 80 gm |
| Potassium ferrocyanide | 24 gm |
| Sodium hydroxide | 12 gm |
| Polyethylene glycol (M.W. Approx. 3500) | 400 gm |
| Polyethylene glycol (M.W. Approx. 7000) | 2,400 gm |
| Methyl paraben | 40 gm |
| Ethyl paraben | 20 gm |
| Bovine serum albumin (BSA) Fraction V | 80 gm |
| Tetracycline | 12 gm |
| Streptomycin | 20 gm |
| Penicillin | 20 gm |
| Neomycin | 12 gm |
| NaOH or HCl | q.s. to pH 7.0 ± .02 |
| NaCl or Distilled Water | q.s. to conductivity 10,300–10,600 |

All of the chemicals listed above are available from Sigma Chemical, St. Louis, Mo. For best results, the components of the synthetic plasma base listed in the table are added in the order listed. The complete formulation is then filtered through a 0.2μ cartridge filter.

The high molecular weight polymer component of the ESR control is intended to contribute to sedimentation of the red blood cells in the suspension by causing increased Rouleaux formation. In this way, the high molecular weight polymer functions similar to an abnormal increase of the Fibrinogen, Alpha 1 and Alpha 2 globulins which perform the same function in whole blood as noted above. It has been found that a high density inert molecule that is physiologically compatible with red blood cells will tend to increase the aggregation of red blood cells in such a manner. Increased aggregation of red blood cells is believed to be caused by the polymer component of the ESR control due to the same physical and electrical mechanism by which the plasma proteins and colloids contribute to red cell aggregation in whole blood.

In the preferred embodiment, Dextran having a molecular weight of substantially between 15,000 and 500,000 is utilized as the high molecular weight polymer, though those skilled in the art will appreciate that other high density inert molecules might alternatively be used. Dextran is a polysaccharide having a chain-like structure comprising a combination of certain polymers of glucose. It is produced from sucrose by Leuconostoc bacteria. Dextran is stable to heat and storage and is soluble in water, making very viscous solutions. Dextran is known for its use as a blood plasma substitute or expander, and particularly for its use in this regard for cell separations.

Dextran has been found to be a preferred material for use in the ESR control because it causes Rouleaux formation while maintaining cell membranes and cell morphologies intact. However, it is proposed that the following additional polymers may be found to provide adequate results in the ESR control:

1. Ficoll (MW 70,000–400,000): A synthetic polymer made by copolymerization of sucrose and epichlorhydrin that is widely used as a density gradient centrifugation medium. It is also used as an immunologically inert carrier for low-molecular-weight haptens in immunological studies.

2. Cellulose: A high-molecular-weight polysaccharide comprising long unbranched chains of (1,4)-linked β-D-glucose residues. Cellulose is found in cell walls of higher plants and some fungi as microfibrils, in which the cellulose chains form crystalline micelles separated by regions of randomized amorphous cellulose.

3. Cyclodextrin: Any of a number of oligosaccharides based on glucopyrinose units that are linked to form a ring structure. The molecule consists of an apolar, electron-rich, hydrophobic interior with exterior sites available for hydrophilic interactions at the entrances to the internal cavity.

4. Agar: A complex polysaccharide produced by red algae. It contains the polysaccharides agarose and agaropectin. Agar is used in food manufacture and as a matrix for the culture of microorganisms.

5. Agarose: A polysaccharide gum obtained from seaweed composed of alternating (1,3)-linked D-galactose and (1,4)-linked 3,6-anhydro-D-galactose residues, as well as small amounts of D-xylose. Some of the D-galactose units are methylated at C-6. Agarose is used as a gel medium in chromatography or electrophoresis.

6. Starch: A high-molecular-weight polysaccharide consisting largely of D-glucose units linked through an α-(1,4)-link, forming a spiral chain with only one terminal reducing moiety per chain. It consists of two fractions: amylose (25 percent) and amylopectin (75 percent). It is the major storage carbohydrate in higher plants, where it accumulates in the form of grains.

7. Polyvinylpyrolidone (PVP) (MW 10,000–360,000).

8. Polyethylene glycol (MW 200–20,000).

9. Percoll: A colloidal PVP coated with silica, used for cell separation and for tissue cultures.

10. Dimethylpolysiloxane (MW 770–116,500).

Those skilled in the art will recognize that other and further polymers in addition to the polymers described above would be suitable for use in the ESR control. The function of the high molecular weight polymer component of the ESR control is to increase red cell aggregation and to thereby contribute to red cell sedimentation. Accordingly, it is believed that any high density inert molecule that is physiologically compatible with red cells would be suitable for use in the ESR control. Those specific examples provided herein are intended to illustrate the types of molecules suitable for use, rather than to limit them.

The final component of the ESR control is mammalian red blood cells. A wide range of sizes of red blood cells are suitable for use in the ESR control, and typically the cell sizes will range over a standard Gaussian distribution curve having an MCV of about 85 cubic microns. This range of cell sizes is not critical, but is utilized in the preferred embodiment because the range approximates that of normal cells present in a drawn sample of human blood. In the preferred embodiment, the mammalian red blood cells are pre-treated by performing approximately three washings of the cells in the synthetic plasma base over an approximately 21 day period. Pre-treatment of the red blood cells stabilizes the cells and causes the cells to maintain their morphology such that the ESR control is stable over an extended period of time.

The following is an example of a method of making an ESR control in accordance with the present invention. As will be more fully discussed below, the molecular weights, concentrations, Hematocrit values and compositions are intended for exemplary purposes only, and are in no way intended to limit the scope of the present invention.

The method comprises the following:

1. Prepare a 3% solution of Dextran (MW 184,000) in the synthetic plasma base. For example, add 30 grams of Dextran powder to 1000 ml of synthetic plasma base. The suspension should be mixed for at least 3 hours on a rotating mixer or with a magnetic mixer. Visually confirm that the powdered Dextran has dissolved.

2. Combine units of pre-treated red blood cells to approximate 1 liter. Centrifuge the units of pre-treated cells at 2000 rpm for 30 minutes at 5°–10° C. Extract as much of the supernatant necessary to yield a RBC count of 900,000 to 1,000,000 per cubic millimeter. (If no cell counter is available, utilize a microhematrocrit centrifuge to verify a Hematocrit of 80% or more.)

3. Utilizing a graduated cylinder, pour 200 ml of the concentrated pre-treated red blood cells and q.s. to 1000 ml of the 3% Dextran/synthetic plasma base mixture. (Note: Each time the 3% Dextran/synthetic plasma base mixture is used, it should be mixed by inversion, e.g. 10–15 times. This is a 2 phase suspension that will separate upon standing.)

4. Perform a Spun Hematocrit on the three component mixture and verify that it has a Spun Hematocrit of 20%±1%. (Note: Each time the finalized product is tested for Hematocrit readings, be sure to mix by gentle inversion, e.g. 10–15 times. This is a 3 phase suspension that will separate upon standing.)

5. Pour the three phase suspension into a container which will accommodate greater than one liter. Make adjustments to the mixture by the addition of concentrated red blood cells or 3% Dextran/synthetic plasma base mixture. This is a trial and error step that may require several additions to achieve the desired 20% Hematocrit value.

6. Keep the finished mixture refrigerated for 24 hours and verify that the Hematocrit is stabilized at 20%±1%.

The ESR control produced by the foregoing process has been found to provide ESR readings in a "High Normal" range. It has also been found that an "Abnormal" range of ESR readings are observed where the foregoing procedure is altered by changing the amount of concentrated pre-treated red blood cells added to 1000 ml of the 3% Dextran/ synthetic plasma base mixture in step 3 from 200 ml to 150 ml, and then performing a Spun Hematocrit on the mixture in step 4 to obtain a Spun Hematocrit of 15%±1%. Other levels of control are obviously possible by simply varying the amount of concentrated red blood cells used in step 3 to obtain different Spun Hematocrit values of the final product.

The ESR control produced by the foregoing method is a stable three-phase suspension which behaves in a fairly predictable manner when used as a control in an ESR test. For example, Tables 2 and 3 below list the results (in mm) of precision studies performed using the two assay levels, "High Normal" and "Abnormal", described above. Further, the tables provide results of ESR tests using the two levels of control with several manufacturer's testing apparatuses, two different testing methods (Westergren and Wintrobe), and two different tube materials (glass and plastic):

TABLE 2

ESR Readings of "High Normal" Assay Level
(Tests run at temperatures ranging 19° C.–21° C.)

| MFR: | LP Italiana | Baxter | Baxter | Ulster | Baxter |
|---|---|---|---|---|---|
| METHOD: | Westerg. | Westerg. | Westerg. | Wintrobe | Wintrobe |
| MTL: | Plastic | Plastic | Glass | Plastic | Glass |
| | 10 | 7 | 15 | 11 | 4 |
| | 9 | 8 | 14 | 10 | 5 |
| | 12 | 8 | 12 | 7 | 5 |
| | 6 | 3 | 12 | 6 | 5 |
| | 11 | 3 | 14 | 10 | 6 |
| | 10 | 6 | 13 | 3 | 2 |
| | 3 | 4 | 12 | 66 | 3 |
| | 5 | 4 | 13 | 2 | 3 |
| | 5 | 9 | 14 | 7 | 4 |
| | 9 | 7 | 12 | 3 | 4 |
| | 9 | 6 | 13 | 4 | 4 |
| | 8 | 4 | 13 | 3 | 4 |
| | 10 | 5 | 10 | 5 | 4 |
| | 7 | 3 | 13 | 4 | 3 |
| | 11 | 8 | 12 | 3 | 4 |
| | 6 | 3 | 16 | 3 | 2 |
| | 8 | 4 | 12 | 6 | 3 |
| | 8 | 5 | 16 | 3 | 3 |
| | 9 | 3 | 14 | 6 | 3 |
| | 13 | 6 | 15 | 8 | 2 |
| | 3 | 8 | 15 | 8 | 4 |
| | 10 | 8 | 10 | 6 | 4 |
| | 5 | 5 | 13 | 6 | 3 |
| | 3 | 5 | 11 | 3 | 3 |
| | 5 | 4 | 15 | 5 | 4 |
| | 5 | 5 | 15 | 2 | 7 |
| | 3 | 6 | 13 | 6 | 7 |
| | 2 | 6 | 13 | 3 | 4 |
| | 9 | 3 | 8 | 5 | 4 |
| | 8 | 3 | 12 | 7 | 6 |
| | 12 | 6 | 12 | 3 | 3 |
| | 7 | 2 | 7 | 2 | 3 |
| | 4 | 7 | 12 | | 4 |
| | 9 | 6 | 13 | | 5 |
| | 6 | 7 | 11 | | 6 |
| | 5 | 5 | 15 | | 5 |
| | 5 | 5 | 12 | | 4 |
| | 9 | 4 | 14 | | 3 |
| | 10 | 2 | 11 | | 5 |
| | 7 | 6 | 14 | | |
| | 4 | 8 | | | |
| | 4 | 4 | | | |
| | | 8 | | | |
| | | 6 | | | |
| NUMBER: | 42 | 44 | 40 | 32 | 39 |
| MEAN: | 7 | 5 | 13 | 5 | 4 |
| S.D.: | 3 | 2 | 2 | 2 | 1 |
| C.V.: | 8.3 | 3.5 | 3.8 | 6.0 | 1.6 |

TABLE 3

ESR Readings of "Abnormal" Assay Level
(Tests run at temperatures ranging 19° C.–21° C.)

| MFR: | LP Italiana | Baxter | Baxter | Ulster | Baxter |
|---|---|---|---|---|---|
| METHOD: | Westerg. | Westerg. | Westerg. | Wintrobe | Wintrobe |
| MTL: | Plastic | Plastic | Glass | Plastic | Glass |
| | 24 | 24 | 32 | 26 | 24 |
| | 23 | 26 | 34 | 22 | 26 |
| | 24 | 24 | 33 | 27 | 26 |
| | 31 | 27 | 24 | 27 | 22 |
| | 30 | 26 | 25 | 26 | 24 |
| | 32 | 23 | 27 | 23 | 23 |
| | 33 | 20 | 29 | 22 | 28 |
| | 32 | 25 | 29 | 23 | 24 |
| | 30 | 23 | 30 | 25 | 25 |
| | 30 | 24 | 31 | 26 | 29 |
| | 36 | 26 | 32 | 27 | 24 |
| | 29 | 23 | 30 | 28 | 27 |
| | 24 | 25 | 33 | 24 | 25 |
| | 28 | 24 | 30 | 25 | 27 |
| | 20 | 27 | 32 | 29 | 26 |
| | 28 | 23 | 24 | 27 | 20 |
| | 22 | 29 | 28 | 25 | 25 |
| | 18 | 27 | 31 | 25 | 22 |
| | 27 | 26 | 28 | 28 | 27 |
| | 24 | 30 | 27 | 29 | 25 |
| | 25 | 31 | 29 | 24 | 31 |
| | 25 | 22 | 31 | 25 | 30 |
| | 25 | 25 | 32 | 21 | 31 |
| | 25 | 23 | 34 | 28 | 32 |
| | 24 | 30 | 36 | 21 | 25 |
| | 25 | 27 | 27 | 25 | 24 |
| | 27 | 24 | 32 | 31 | 27 |
| | 22 | 26 | 31 | 25 | 21 |
| | 25 | 25 | 29 | 23 | 26 |
| | 25 | 24 | 25 | 25 | 27 |
| | 22 | 25 | 31 | 25 | 19 |
| | 23 | 17 | 30 | 27 | 22 |
| | 28 | 25 | 29 | 34 | 24 |
| | 25 | 25 | 27 | 25 | 24 |
| | 23 | 26 | 27 | 25 | 22 |
| | 25 | 23 | 25 | 26 | 26 |
| | 27 | 22 | 31 | 26 | 20 |
| | 24 | 21 | 34 | 24 | 22 |
| | 25 | 22 | 30 | | 23 |
| | 28 | 25 | 21 | | 23 |
| | 25 | 22 | 21 | | 25 |
| | 25 | 20 | 22 | | 22 |
| | | 15 | | | |
| | | 25 | | | |
| | | 27 | | | |
| | | 22 | | | |
| | | 22 | | | |
| | | 26 | | | |
| | | 19 | | | |
| | | 22 | | | |
| | | 26 | | | |
| | | 21 | | | |
| NUMBER: | 42 | 52 | 42 | 38 | 42 |
| MEAN: | 26 | 24 | 29 | 25 | 25 |
| S.D.: | 4 | 3 | 3 | 3 | 3 |
| C.V.: | 13.0 | 9.2 | 11.9 | 6.5 | 9.0 |

Using components having the molecular weight, concentrations, Hematocrit values and compositions in the method of the preceding examples will produce an ESR control in accordance with the present invention. However, significant departures from those values are possible while still remaining within the scope of the present invention. For example, in the following three examples, in which the Hematocrit value, Dextran concentration, and Dextran molecular weight are all varied, it is believed that the resulting suspensions will all produce an ESR control that provides an ESR reading of about 30 for a given test apparatus:

| HEMATOCRIT VALUE | DEXTRAN CONCENTRATION | DEXTRAN MW | ESTIMATED APPROX. ESR VALUE |
|---|---|---|---|
| 30 | 8% | 280,000 | 30 |
| 25 | 5% | 240,000 | 30 |
| 15 | 3% | 140,000 | 30 |

The purpose of the preceding examples is to demonstrate that it is the relative values of the Hematocrit, Dextran concentration and Dextran molecular weight utilized in the ESR control, rather than the values themselves, that are important to the effectiveness of the suspension as an ESR control. The purpose of the ESR control is to produce results in a predictable range of ESR values; accordingly, as long as the composition is such that consistent ESR values are obtained, the composition is useful as an ESR control. Those skilled in the art will recognize that other and further variations of the values listed above are possible.

While the above description contains many specificities, these should not be construed as limitations on the scope of the invention, but rather as an exemplification of a preferred embodiment thereof. Other variations are possible.

Accordingly, the scope of the present invention should be determined not by the embodiments illustrated above, but by the appended claims and their legal equivalents.

What is claimed is:

1. A method of monitoring the accuracy and precision of an erythrocyte sedimentation rate (ESR) test apparatus and method, comprising the steps of:

a. providing an erythrocyte sedimentation rate control capable of producing measured ESR values within a predictable range;

b. providing an erythrocyte sedimentation rate test apparatus;

c. performing an erythrocyte sedimentation rate (ESR) determination using said erythrocyte sedimentation rate control and said erythrocyte sedimentation rate test apparatus; and d. comparing the ESR determination performed in step c. with the predicted range of ESR values expected from the erythrocyte sedimentation rate control.

2. The method of claim 1, wherein said erythrocyte sedimentation rate control comprises a synthetic plasma base.

3. The method of claim 1, wherein said erythrocyte sedimentation rate control comprises mammalian red blood cells.

4. The method of claim 3, wherein said erythrocyte sedimentation rate control further comprises an aggregating agent for aggregating said mammalian red blood cells.

5. A method of verifying the legitimacy of an analytical method for determining the sedimentation rate of erythrocytes in blood specimens; comprising the steps of:

providing a material capable of producing reproducible sedimentation rate measurements in an erythrocyte sedimentation rate test apparatus, providing an erythrocyte sedimentation rate test apparatus, performing a sedimentation rate test using said material and said erythrocyte sedimentation rate test apparatus, and comparing the sedimentation rate test of said performing step with a predicted range of sedimentation rate values expected from the material.

6. The method of claim 5, wherein said material comprises:

a synthetic plasma base, mammalian red blood cells suspended in said synthetic plasma base, and an aggregating agent in solution with said synthetic plasma base and said mammalian red blood cells, said aggregating agent having a molecular weight and concentration sufficient to cause a reproducible sedimentation rate of said red blood cells in said synthetic plasma base.

7. The method of claim 5, wherein said material comprises a synthetic plasma base.

8. The method of claim 5, wherein said material comprises mammalian red blood cells.

9. The method of claim 8, wherein said material further comprises an aggregating agent for aggregating said mammalian red blood cells.

\* \* \* \* \*